(12) United States Patent
Schleyer et al.

(10) Patent No.: US 12,387,393 B2
(45) Date of Patent: Aug. 12, 2025

(54) MAGNETIC RESONANCE HARDWARE-CONTRIBUTED ATTENUATION IN POSITRON EMISSION TOMOGRAPHY

(71) Applicant: Siemens Medical Solutions USA, Inc., Malvern, PA (US)

(72) Inventors: Paul Schleyer, Knoxville, TN (US); Emily Anaya, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 461 days.

(21) Appl. No.: 18/004,455

(22) PCT Filed: Apr. 30, 2021

(86) PCT No.: PCT/US2021/070489
§ 371 (c)(1),
(2) Date: Jan. 6, 2023

(87) PCT Pub. No.: WO2022/056501
PCT Pub. Date: Mar. 17, 2022

(65) Prior Publication Data
US 2023/0298231 A1 Sep. 21, 2023

Related U.S. Application Data

(60) Provisional application No. 62/706,806, filed on Sep. 11, 2020.

(51) Int. Cl.
*G06T 11/00* (2006.01)
*A61B 6/00* (2024.01)
(Continued)

(52) U.S. Cl.
CPC ............ *G06T 11/005* (2013.01); *A61B 6/037* (2013.01); *A61B 6/4417* (2013.01);
(Continued)

(58) Field of Classification Search
CPC ............ G06T 11/005; G06T 7/75; G06T 2207/10024; G06T 2207/20081;
(Continued)

(56) References Cited

U.S. PATENT DOCUMENTS

| | | |
|---|---|---|
| 2009/0105583 A1 | 4/2009 | Martin et al. |
| 2010/0156421 A1 | 6/2010 | Sukkau |

(Continued)

OTHER PUBLICATIONS

Frohwein et al.; PET attenuation correction for flexible MRI surface coils in hybrid PET/MRI using a 3D depth camera; published on Jan. 17, 2018; Physics in Medicine & Biology, vol. 63, No. 2; p. 1-13 (Year: 2018).*

(Continued)

*Primary Examiner* — Chao Sheng

(57) ABSTRACT

PET imaging (406) accounts for attenuation by MR hardware (110). A camera (112) captures the MR hardware (110) as positioned on or by the patient (116). For example, MR local coils to be or as positioned between the emission sources in the patient (116) and the PET detector are optically imaged (402). Image processing is used to determine (404) the position of the MR hardware (110). The attenuation of the MR hardware (110) is accounted for in attenuation correction for PET imaging (402) based on the determined position.

20 Claims, 4 Drawing Sheets

(51) Int. Cl.
  *A61B 6/03* (2006.01)
  *A61B 6/04* (2006.01)
  *G01R 33/34* (2006.01)
  *G01R 33/48* (2006.01)
  *G06T 7/73* (2017.01)

(52) U.S. Cl.
  CPC ...... *A61B 6/5282* (2013.01); *G01R 33/34084* (2013.01); *G01R 33/481* (2013.01); *G06T 7/75* (2017.01); *A61B 6/0407* (2013.01); *G06T 2207/10024* (2013.01); *G06T 2207/20081* (2013.01); *G06T 2207/30004* (2013.01); *G06T 2207/30204* (2013.01)

(58) Field of Classification Search
  CPC . G06T 2207/30004; G06T 2207/30204; A61B 6/037; A61B 6/4417; A61B 6/5282; A61B 6/0407; G01R 33/34084; G01R 33/481

See application file for complete search history.

(56) References Cited

U.S. PATENT DOCUMENTS

2011/0317900 A1 12/2011 Pal et al.
2018/0081014 A1* 3/2018 Li .................. G01R 33/481

OTHER PUBLICATIONS

International Search Report for Corresponding PCT AppIn No. PCT/US2021/070489, dated Aug. 2, 2021.
Evaluating the Accuracy of Single Camera Calibration. Accessed Apr. 8, 2021. pp. 1-5. https://www.mathworks.com/help/vision/examples/evaluating-the-accuracy-of-single-camera-calibration.html.
Luhmann, Thomas. "Eccentricity in images of circular and spherical targets and its impact on spatial intersection." The Photogrammetric Record 29.148 (2014): 417-433.
Otepka, Johannes O., and Clive S. Fraser. "Accuracy enhancement of vision metrology through automatic target plane determination." (2004): 873-879.
Yao, Ningshi, et al. "Monocular vision-based human following on miniature robotic blimp." 2017 IEEE International Conference on Robotics and Automation (ICRA). IEEE, 2017. pp. 1-6.

* cited by examiner

MAGNETIC RESONANCE HARDWARE-CONTRIBUTED ATTENUATION IN POSITRON EMISSION TOMOGRAPHY

RELATED APPLICATION

The present patent document claims the benefit of the filing date under 35 U.S.C. § 119(e) of Provisional U.S. Patent Application Ser. No. 62/706,806, filed Sep. 11, 2020, which is hereby incorporated by reference.

BACKGROUND

The present embodiments relate to positron emission tomography (PET). In PET, attenuation information is used in reconstruction. Typically, the attenuation is derived from a computed tomography (CT) scan.

For a combination system of magnetic resonance (MR) and PET, the MR hardware may attenuate emissions for PET, and CT may be unavailable, at least to detect attenuation from MR hardware. To acquire MR images, local coils may be placed close to the surface of the patient. In most MR acquisition sequences, the coils are not visible in the MR image. In combined PET and MR systems, the coil and coil-housing materials attenuate the 511 keV photons that are emitted from the patient and used to create the PET image.

For some rigid and non-deformable coils (e.g., the head-neck coil), the material is physically attached to the patient table in a fixed location and the 3D location and an orientation is therefore assumed. However, the true position may vary slightly from the assumed position due to the tolerances of the patient table positioning and the mechanism that attaches the coil to the table. Some MR coils are not placed in known positions or orientations. For example, flexible local coils are placed on the patient differently for each acquisition and are usually physically curved around the patient's body. The location, orientation, and deformation of the coil is unknown. For attenuation correction in PET imaging, the MR-invisible coils are ignored despite attenuating the photons. Due to unknown positioning, no attenuation correction of this material is performed and approximate errors in PET activity concentration of up to 10% may occur due to some coils.

SUMMARY

By way of introduction, the preferred embodiments described below include methods, systems, and non-transitory computer readable media for PET imaging that accounts for attenuation by MR hardware. A camera captures the MR hardware as positioned on or by the patient. For example, MR local coils to be or as positioned between the emission sources in the patient and the PET detector are optically imaged. Image processing is used to determine the position of the MR hardware. The attenuation of the MR hardware is accounted for in attenuation correction for PET imaging based on the determined position.

In a first aspect, a method is provided for PET imaging that accounts for attenuation by MR hardware. An optical camera images the patient. The imaging captures an image of the patient and the MR hardware. An attenuation coefficient map for the MR hardware relative to the patient is generated from the image. PET imaging uses attenuation correction based, at least in part, on the attenuation coefficient map for the MR hardware.

In one embodiment, the patient is imaged with the camera outside a bore of a combination PET and MR imaging system. The camera is directed to a patient bed of the combination PET and MR imaging system. For example, the patient is imaged while the patient is outside the bore.

In another embodiment, one or more optical fiducials on the MR hardware are imaged. A position of the MR hardware relative to the patient is determined from the optical fiducials.

A template map of attenuation of the MR hardware may be used. The attenuation coefficient map of the MR hardware as positioned for the patient is generated from the template map of attenuation of the MR hardware. In one embodiment, the MR hardware is a flexible local coil. The template is adapted to reflect a positioning of the flexible local coil on the patient. For example, the adaptation recognizes shapes and locations of markers of the flexible local coil in the image. Three-dimensional locations of the markers are determined from the shapes and locations. The template is fit to the three-dimensional locations. As another example, the three-dimensional locations of markers of the flexible local coil are predicted by a machine-learned model receiving the image as input. The template is fit to the three-dimensional locations. In another embodiment, a machine-learned model receiving the image as input directly outputs the attenuation coefficient map as fit to the patient.

More than one camera may be used. The patient is imaged with the optical camera and at least one additional optical camera. The attenuation coefficient map is generated from the image and at least one additional images from the at least one additional optical camera. In some embodiments, one or more three-dimensional positions of the MR hardware are identified from the image using a color-coded marker and/or a visible pattern on the MR hardware.

In one embodiment, at least a portion of the patient is reconstructed from emissions. The reconstruction uses the attenuation correction where the attenuation coefficient map for the MR hardware is included with attenuation for the portion of the patient.

In a second aspect, a medical imaging system includes a positron emission tomography imager and a magnetic resonance imager configured to image a patient using one or more local coils positioned on a patient. A camera is configured to capture an image of the patient and the one or more local coils as positioned on the patient. A processor is configured to correct for attenuation of the one or more local coils based on one or more positions, respectively, identified from the image. The correction is for imaging by the positron emission tomography imager.

In a further embodiment, the positron emission tomography imager and the magnetic resonance imager share a bore for imaging the patient. The camera is mounted outside the bore and the image is captured while the patient is mostly outside the bore.

In one embodiment, the one or more local coils comprise flexible local coils. The processor is configured to identify the one or more positions as three-dimensional positions from markers on the one or more local coils.

In other embodiments, the processor is configured to generate an attenuation coefficient map from a fit of template attenuation coefficient maps to the three-dimensional positions.

In a third aspect, a method is provided for PET imaging that accounts for attenuation by a MR local coil. An optical image of the MR local coil as positioned on the patient is captured. A distribution of attenuation from the MR local coil is determined based on the optical image. A PET image is reconstructed from emissions where the reconstruction includes attenuation correction using the distribution of the attenuation from the MR local coil.

In one embodiment, markers on the MR local coil are located from the optical image, and an attenuation template is fit to the located markers. In other embodiments, the distribution information is output from a machine-learned model in response to input of the optical information. For example, a spatial transform for the template, the template as deformed, and/or the marker locations are output. In yet other embodiments, a deformation and a position of the MR local coil as positioned on the patient for MR imaging are determined. The distribution of attenuation is based on the deformation and the position of the MR local coil.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The attenuation of MR hardware can be corrected by using a spatial distribution of attenuation coefficients. The precise three-dimensional (3D) location and orientation of the coil is determined to find the spatial distribution of the attenuation by the MR hardware relative to PET/MR imaging coordinates. Spatial orientation and deformation of MR hardware is determined from optical camera or cameras and provided for PET attenuation correction. The 3D location, orientation, and deformation of MR coils is determined from the camera image for accurate PET attenuation correction, providing attenuation correction of otherwise position-unknown MR coils for PET imaging. For example, one or more optical images (e.g., two-dimensional (2D) images) are used to create an attenuation correction map of a deformable, PET-invisible and MR-invisible MR coil in an unknown location and deformation save for the camera imaging.

Optical cameras are low cost off-the-shelf devices, providing a cost-effective way to account for MR hardware attenuation. Similarly, markers used to assist the image processing are simple and cheap to manufacture. The MR hardware, other than attaching visible markers, does not need to be modified. The markers are not visible in and do not distort PET or MR images. MR or PET detectable markers are not needed, avoiding sources of phase wrap, image artifacts, or additional sources of radiation.

Figure 1:
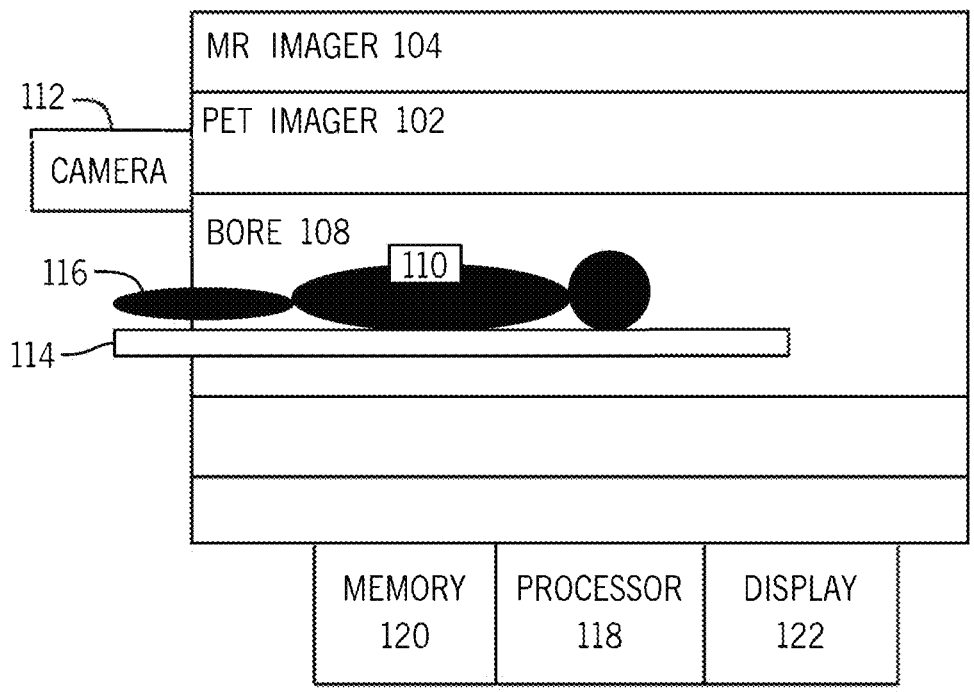
FIG. 1 is a block diagram of a system, according to one embodiment, for accounting for attenuation of MR hardware in PET imaging.

FIG. 1 shows a medical imaging system. For example, a PET-MR system reconstructs in PET while accounting for attenuation correction from MR hardware. The MR hardware may attenuate photons in PET imaging, so an optical camera 112 is used to determine a distribution of attenuation contributed by intervening MR hardware. The medical imaging system performs the method of FIG. 4 or another method to reconstruct and PET image while correcting for the attenuation from MR hardware.

The PET-MR system includes a MR scanner or imager 104, a PET scanner or imager 102, the camera 112, and a bed 114 for the patient 116. A computed tomography system is not provided but may be included, such as in a same room or facility without sharing a common bore 108. The processor 118, memory 120, and/or display 122 are part of the PET imager 102, the MR imager 104, or are separate (e.g., a computer or workstation). Additional, different, or fewer components may be provided. For example, the system is a computer without the MR imager 104 and/or PET imager 102. As another example, the medical system includes power supplies, communications systems, and user interface systems.

The bed 114 is a gurney, table, or other support to hold an examination subject, such as a patient. A robot, gears, cable, track, and/or other device move the bed 114. The movement is along an axial dimension but may include other directions of movement, such as up and down. The MR imager 104 and PET imager 102 share a housing (e.g., gantry) and the bed 116. The bore 108 formed for scanning the patient using MR and/or PET is cylindrical or other shape and shared by the PET imager 102 and the MR imager 104. The bed 114 moves the patient 116 into the bore 108 for and/or during PET and/or MR imaging.

The PET imager 102 is a nuclear imaging system. The PET imager 102 includes a ring of detectors such as scintillation crystals coupled to avalanche photo diodes. Solid-state or semiconductor detectors may be used. The detectors detect gamma rays emitted indirectly by a positron-emitting tracer. Pairs of gamma rays generated by a same positron may be detected using the ring of the detectors. The pairs of gamma rays travel about 180 degrees apart. If the direction of travel intersects the arrangement of detectors at two locations, a coincident pair may be detected. To distinguish specific pairs, the coincidence of detected gamma rays is determined. The timing of receipt is used to pair the detected gamma rays. The timing, as prompt data, may also indicate the time-of-flight, providing information generally about where along a line of response the emission occurred. Based on the detected event, a line-of-response is determined given the detectors involved in the detection of that event.

The detected events are passed to the memory 120 and/or processor 118. The processor 118 connects with the detectors 16, such as through the coincidence processors. The processor 118 also connects with the MR system 104 to receive information from MR scanning of the patient before, during, and/or after the PET scanning.

The tissues of the patient 116 and any other material between the emission and the detectors may attenuate the gamma radiation. The PET imaging or reconstruction is more accurate by accounting for this attenuation. An attenuation model of the patient fit to the MR data or attenuation determined from an MR scan of the patient provides the attenuation information from the patient. MR hardware between the patient and the PET detectors may cause attenuation. The processor 118 also accounts for the attenuation by the MR hardware in the PET reconstruction.

The MR imager 104 includes a main magnet for generating a generally uniform main magnetic field in the bore 108. A whole body coil and gradient coils are also included. The whole-body coil may not be included. The MR imager 104 may include local coils, such as a coil with a rigid or stiff housing with or without hinges. The local coil is positioned on, against, or adjacent to (e.g., within 6 inches) of the patient 116. In one embodiment, one or more flexible or "blanket" type local coils 110 are used. This local coil 110 is positioned on or under the patient and conforms, at least partly, to the patient 116 due to flexibility. The local coils 110 may include substrate, housing, electronics, cables, antenna, and/or other gamma radiation attenuating material. Other MR hardware, such as cables, may be in the bore 108 between the patient and at least some of the detectors of the PET imager 102.

The MR imager 104 is configured to image the patient 116 using one or more local coils 110, whether flexible or fixed, positioned on the patient 116. Radiofrequency pulses are transmitted by the MR imager 104, such as by a whole-body coil under spatial control of gradient coils. The local coils 110 are used to receive radiofrequency signals generated as spins of molecules shifted by the transmitted pulses realign to the main magnetic field.

The MR imager 104 is within a same housing as the PET imager 102 or is spaced apart by and connected by a common track for the bed 114. Completely separate MR imager 104 and PET imager 102 may be used. The local coil 110 or other MR hardware may be left on the patient 116 during PET imaging even with separate imaging systems (e.g., not a combined system or no shared housing and/or bed 114).

To account for attenuation of the MR hardware, such as the flexible local coils 110, in PET imaging, markers to make the MR hardware detectable are added to the MR hardware. For PET detection, the markers would need to emit radiation, which is not desired. Since the MR hardware is used in MR imaging, the MR hardware is typically not detectable by the MR imager 104 to avoid imaging artifacts. Instead, the camera 112 detects the MR hardware.

The camera 112 is an optical camera, such as a CCD or solid state camera. The camera 112 captures a two-dimensional image or video. In other embodiments, a depth camera, stereo camera system, structured light, time-of-flight, and/or three-dimensional imaging camera is used.

Figure 2:
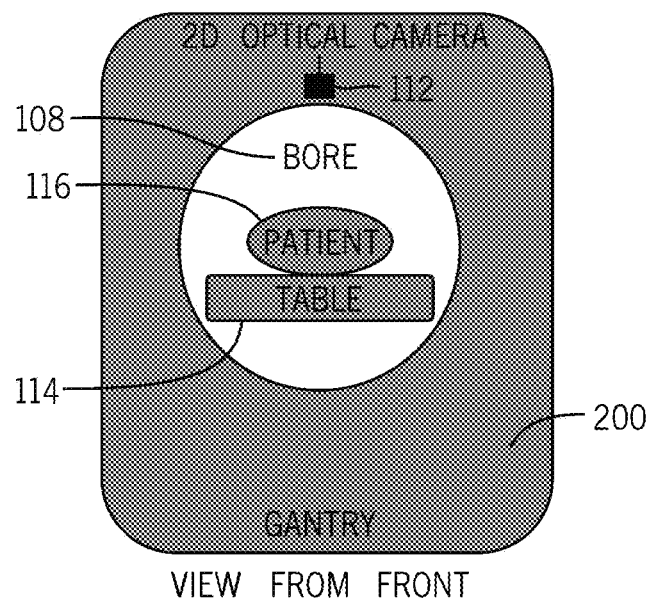
FIG. 2 is a front view of an example medical imaging system including a camera for attenuation estimation.

The camera 112 is mounted in a same room as the PET imager 102 and/or MR imager 104. For example and as shown in FIGS. 1 and 2, the camera 112 is connected to the gantry 200 or housing at one end of the bore 108, such as above the patient 116 and the bed 114. The camera 112 capture images of the patient 116 before positioning in the bore 108, such as while the patient is mostly outside of the bore 108. For example, the camera 112 is directed downward with a field of view mostly or entirely outside of the bore 108 to capture the patient 116 before starting to move into the bore 108 or as the patient 116 is moved into the bore 108. The camera 112 may be angled to capture the patient 116 within the bore 108.

In one embodiment, the optical camera 112 is mounted on the gantry 200 outside the bore 108. Multiple cameras 112 may be provided for stitching together a larger field of view and/or redundancy. The camera 112 is used to create one or more 2D images of the MR hardware (e.g., local coil 110) on the patient 116 prior, during, or after PET images are acquired. In one arrangement, the optical camera 112 is directed to image the patient outside the bore 108 and/or gantry 200. In another arrangement, the optical camera 112 is directed to image the patient inside the bore 108, facilitating optical imaging during PET and/or MR acquisition.

Each camera 112 is calibrated to the patient table 114, gantry 200, or other portion of the medical imaging system. The camera is calibrated by taking images of a checkerboard or other marker, placed flat on the patient table or bed 114 at a certain distance away from the camera 122, at various orientations. Marker locations determined from each camera are combined to improve accuracy and coverage. Camera intrinsics, extrinsics, and/or lens distortion parameters are estimated as part of the calibration. The camera intrinsics includes the focal length of the lens. The focal length is used to determine the spatial location of markers placed on the MR coil 110 after calibration. The intrinsic matrix, rotation matrix, and translation vectors that result from the calibration are used to transform from image space coordinates to world space coordinates.

Once calibrated, the camera 112 may be used to determine the spatial distribution of the MR hardware relative to the PET imager 102. The processor 118 applies image processing to detect the spatial distribution of the MR hardware from one or more captured images from the camera 112. In one embodiment, markers are added or included on the MR hardware to assist in detection. The markers are colored and/or patterned. For example, colored markers are placed on the surface of the MR coil 110 in fixed or known locations. The entire MR coil 110 may be patterned. Structured patterns on the markers may improve accuracy of determining a central location of a marker. The markers are two or three-dimensional, such as being flat stickers, spheres, or cylinders.

Figure 3:
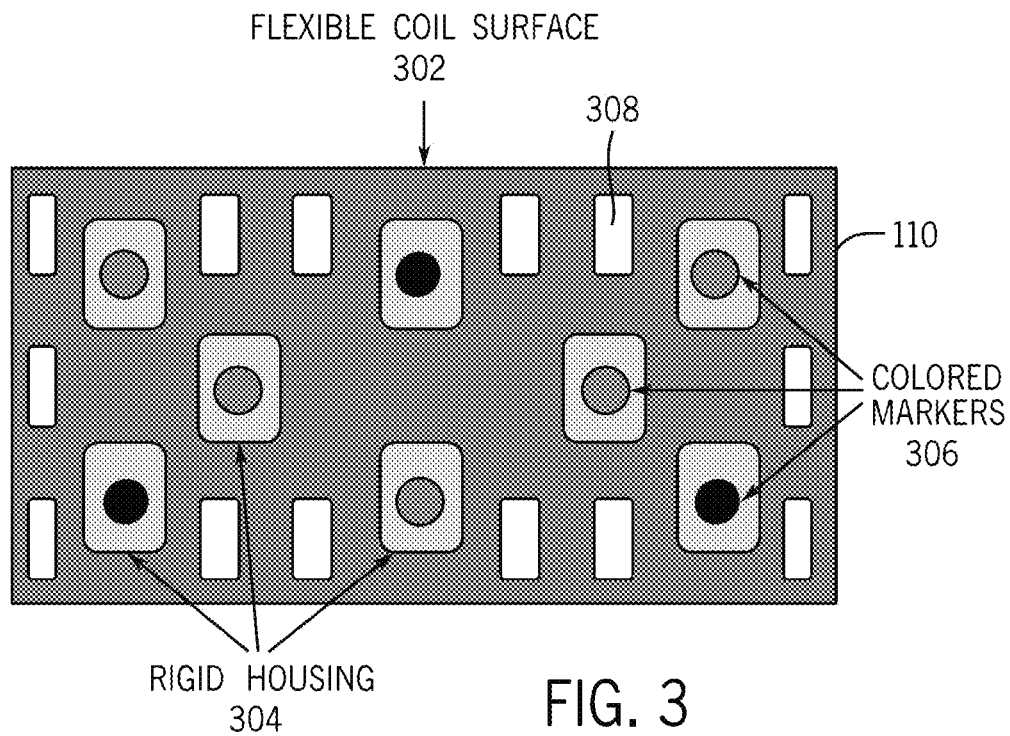
FIG. 3 is a top view of an example flexible local coil for MR.

FIG. 3 shows a top view of one embodiment of a flexible coil 110 to be used with a patient. The local coil 110 includes a substrate having a top surface 302, rigid housings 304 for electronics and/or cabling, the color-coded circular markers 306, and holes 308. Any number and/or positioning of the markers 306 may be used. Other local coils 110 with other marker arrangements may be used.

The processor 118 is a general processor, digital signal processor, graphics processing unit, application specific integrated circuit, artificial intelligence processor, field programmable gate array, digital circuit, analog circuit, combinations thereof, or other now known or later developed device for determining a spatial distribution of MR hardware relative to a patient (or patient table 114) and/or reconstructing in PET imaging while accounting for attenuation of MR hardware. The processor 118 is a single device, a plurality of devices, or a network. For more than one device, parallel or sequential division of processing may be used. Different devices making up the processor 118 may perform different functions, such as one processor for determining spatial distribution of attenuation from MR hardware and another processor for reconstructing the object (i.e., patient) space with attenuation correction. In one embodiment, the processor 118 is a control processor or other processor of the medical imaging system or the PET imager 102. In other embodiments, the processor 118 is part of a separate workstation or computer.

The processor 118 operates pursuant to stored instructions to perform various acts described herein. The processor 118 is configured by software, firmware, and/or hardware to perform any or all of the acts of FIG. 4. The operation and configuration of the processor 118 is first described in general below. An example implementation is described in more detail in the following discussion of FIG. 4.

The processor 118 is configured to reconstruct the activity distribution in PET imaging using the detected emissions along the lines of response. The time of flight (TOF) may be used. Detected emissions along lines of response are used to reconstruct the activity distribution. To account for differences in attenuation due to different tissues and any obstructions along the different lines of response, attenuation correction factors or integrated attenuations along the corresponding lines of response are used in the reconstruction. For some of the lines of response, attenuation may be caused by MR hardware, such as local coils 110. Similarly, the reconstruction may account for scattering using attenuation. Scattering from the MR hardware is accounted for in the reconstruction.

The processor 118 is configured to correct for attenuation of the one or more local coils 110 based on one or more positions, respectively, identified from the image captured by the camera 112. The processor 118 is configured to identify the one or more positions as three-dimensional (3D) positions from markers on the one or more local coils. The 3D positions indicate the location, deformation, and/or orientation of the MR hardware. The processor 118 generates an attenuation coefficient map (attenuation map or attenuation correction factor map) from a fit of a template attenuation coefficient map to 3D positions detected from the camera 112.

The processor 118 uses the events (e.g., line-of-response events or PET data), attenuation data, parameter data, attenuation correction factors (ACF), and/or other information stored in the memory 120 for processing. For processing, the data bypasses the memory 120, is temporarily stored in the memory 120, or is loaded from the memory 120.

The detected events, line-of-response information (e.g., sinograms), time step, prompt data, attenuation information, ACF, reconstructed image, or other data is stored in the memory 120. The data is stored in any format. The memory 120 is a buffer, cache, RAM, removable media, hard drive, magnetic, optical, database, or other now known or later developed memory. The memory 120 is a single device or group of two or more devices. The memory 120 is part of the PET imager 102 or a remote workstation or database, such as a PACS memory.

The memory 120 is additionally or alternatively a non-transitory computer readable storage medium with processing instructions. The memory 120 stores data representing instructions executable by the programmed processor 118 for determining a spatial distribution of MR hardware, determining a spatial distribution of attenuation from MR hardware, and/or reconstructing in PET with attenuation correction based on MR hardware. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The medical imaging system may include the display 122. For example, the processor 118 reconstructs the patient or object being scanned from the line-of-response PET data and the attenuation data. The reconstruction, reconstructed object, or reconstructed activity distribution is used for three-dimensional rendering, multi-planar reconstruction, or two-dimensional imaging of the function of the object or patient 116. The images are displayed on the display 122. The display 122 is a CRT, LCD, plasma screen, projector, printer, or other output device for showing a PET image of the activity distribution. The PET image may be a qualitative or quantitative image.

Figure 4:
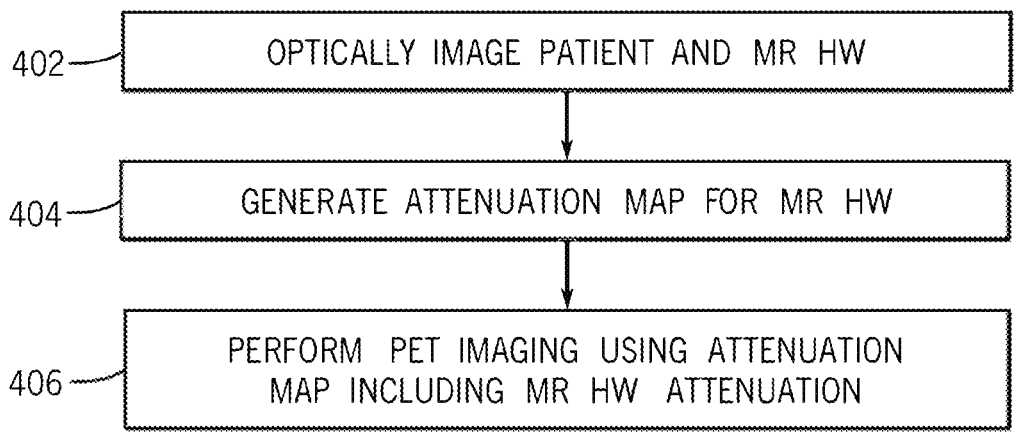
FIG. 4 is a flow chart of an embodiment of a method for PET imaging that accounts for attenuation by MR hardware.

FIG. 4 shows one embodiment of a method for PET imaging that accounts for attenuation by MR hardware, such as a local coil. The distribution of and attenuation caused by the MR hardware relative to the patient and/or PET imager is determined from image processing one or more optical images of the patient and MR hardware. PET reconstruction includes attenuation correction for the distribution of attenuation from the MR hardware, resulting in more accurate PET imaging.

The method of FIG. 4 is implemented by the camera 112, processor 118, PET imager 102, medical imaging system, and/or another component or system. For example, the camera performs act 402, the processor 118 performs act 404, and the PET imager 102 performs act 406 using or without using the processor 118. The resulting PET image is displayed on the display 122. Other components may perform the acts, such as a workstation performing both acts 404 and 406 based on information provided by a camera 112 and a PET imager 102 or memory 120.

Additional, different, or fewer acts may be performed. For example, acts for placing the patient on the bed and the MR hardware relative to the patient are included. As another example, acts for calibrating the camera to the PET-MR imager are provided. The acts are performed in the order shown or a different order. Act 404 may be included as part of act 406.

In act 402, one or more cameras image the patient. The camera or cameras are outside a scan bore of a combination PET and MR imaging system, such as connected to the imaging system housing near an entrance/exit of the bore. One or more cameras may be in the bore or housing of the imaging system in the bore. The camera or cameras are directed to a patient bed of the combination PET and MR imaging system. Alternatively, the images are captured before transfer of the patient to the bed of the PET and/or MR imaging systems or system. The patient with the MR hardware is imaged optically while the patient is outside, inside, or partially inside and outside of the bore.

The camera or cameras capture one or more images of the patient and MR hardware, such as the MR local coil or coils, as positioned on the patient. The MR hardware positioned for MR imaging will be on the patient during PET imaging, so the image or images are captured with the MR hardware as positioned for the PET and MR imaging.

The images are captured before, during, and/or after the PET and/or MR imaging. For example, a camera captures a series of images (e.g., video) of the patient while the bed moves the patient into the bore for MR and PET imaging. The images are stitched together or processed as patches representing different parts of the patient. As another example, multiple cameras capture the patient while outside or mostly outside the bore from different angles, allowing stitching together a representation of the patient from different views. In other examples, multiple cameras have overlapping fields of view or the same field of view, and the images are processed separately for combined (e.g., averaged) results. A single camera with a single image showing at least part of the patient and a MR flexible local coil as the MR hardware is used as one example in further discussion below for FIG. 4.

The captured image is an optical image. Images in infrared or other frequencies may be used. The wavelength or detected signal is different than used for PET or MR imaging.

The captured image represents the patient and MR local coil. To make the MR local coil easier to detect, one or more optical fiducials are on the MR local coil. For example, colored or patterned (crossed lines) circular or other shaped stickers are placed at known or specific positions on the MR local coil. Cylindrical or other shaped 3D markers may be used. Where the local coil may bend or flex and/or due to the three-dimensional surface of the local coil, the markers are displaced relative to each other in three dimensions. The image captures or represents the relative placement of the markers to each other on the MR local coil.

In act 404, a processor generates an attenuation coefficient map for the MR hardware relative to the patient or patient table from the image. The relative placement of the markers (e.g., color-coded markers or visible patterns) and/or distortion of the markers in the image as compared to the known distribution and shape of the markers on the local coil is used to determine the spatial distribution of the local coil on the patient. This spatial distribution provides a distribution of attenuation from the MR local coil based on the optical image. Any deformation and position of the MR local coil as positioned on the patient for MR imaging is used to generate the attenuation coefficient map. The deformation and position of the MR local coil or markers captured in the image indicates the distribution of attenuation. In alternative embodiments, the deformation and position of the MR local coil is determined from the image without markers.

The position in three-dimensions of the MR local coil (or another MR hardware) is determined relative to the patient. The MR local coil is placed on or against the patient. The PET imager images emissions from the patient. By detecting the position relative to the patient, the 3D positioning of the MR local coil in a same coordinate system (e.g., world coordinates) as the PET imager is determined from the image (or images).

The processor generates the attenuation coefficient map (e.g., distribution of attenuation in three dimensions) for the MR local coil as positioned on the patient from the spatial distribution of the local coil. A model or measured attenuation of the local coil is deformed, oriented, and/or positioned to account for the positioning, orientation, and/or deformation of the local coil on the patient. For example, the processor generates the attenuation coefficient map of the MR hardware as positioned in 3D for the patient from a template map of attenuation of the MR hardware.

The model or template attenuation coefficient map may be from actual measurements of attenuation caused by the MR local coil or the type of MR local coil. For example, to generate the template, the markers of the MR local coil temporarily include small attenuating objects (e.g., ball bearings or other objects detectable to computed tomography or other attenuation measurement) to facilitate marker location and orientation. The local coil is laid flat or in another known position in three dimensions. An attenuation coefficient map is created by transmission measurements, such as a rotating rod source of radiation to scan the local coil, Lutetium oxyorthosilicate (LSO) radiation from a PET scan, a CT scan, or some combination of several measurements is performed. The location of the markers is identified in the attenuation coefficient map by locating the small measurement-opaque object (e.g. the ball bearing) on each marker. For circular makers, only a single opaque object is required in the circle center. In other markers, more than one object may be used per marker for creating the attenuation template. Alternatively, simulation or known material properties are used to create the model or template attenuation coefficient map.

The template attenuation coefficient map of the coil is created once. The measurement-opaque objects may then be removed if that local coil is to be used for patients. Other local coils of the same type have markers in the same locations but without the measurement-opaque objects for creating the template. Then, for each patient imaging instance, the template is adapted to create an attenuation coefficient map of the coil on the patient. The template or model of known attenuation for the local coil is altered to reflect the positioning in three dimensions (e.g., position on the patient, orientation on the patient, and/or deformation of the local coil about the patient) of the local coil on the patient for PET and MR imaging.

Various approaches may be used to adapt the attenuation coefficient map. In an analytical approach, the two-dimensional optical image or images of the coil on the patient may be pre-processed, such as filtered or normalized. The spatial location of each marker is calculated from known parameters of the marker shapes. The template attenuation coefficient map is fit to the calculated marker locations. Further refinement of the fit may be performed with a data-driven PET consistency criteria method if the goodness of marker fit is below a threshold. The data-driven PET consistency criteria method treats various PET detected events as point sources and fits the attenuation to the PET measurements.

Figure 5:
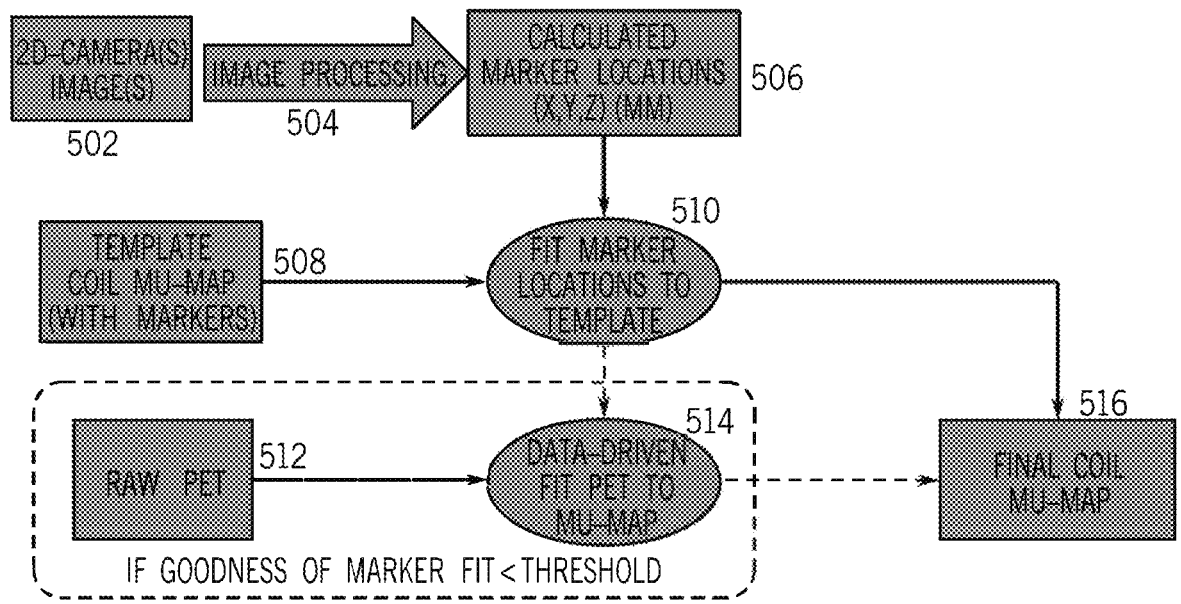
FIG. 5 illustrates an example analytic approach for attenuation template fitting.

FIG. 5 shows an embodiment of an analytical approach. The markers on the MR local coil are located from the optical image 502 by image processing 504. The processor recognizes the shapes and locations of markers of the flexible local coil in the image. Shape recognition algorithms are used to identify the markers in the image. The marker locations 506 in three dimensions are determined as a result of the image processing 504 from the shapes and locations of the markers in the image. For example, for circular markers or straight lines, a Hough Transform is used. The voting space of the Hough transform can be extended to consider non-circular appearance of a two-dimensional (2D) circle projected to a plane when the marker is not normal to the camera axis (i.e., the projected shape of a circle will be oval). For 3D markers, if imaged off the optical axis, the projected appearance in the image plane is also elliptical, however the semi-axes are of more similar length than that of the 2D marker projection. The center of the ellipse is identical to the imaged 2D circle center only when the circle plane is parallel to the image plane. The same is true for the 3D sphere when the sphere is in line with the camera axis. Both the center of the marker and the diameter of the marker in the image are determined in order to find the spatial location of the marker in the world space.

Figure 6:
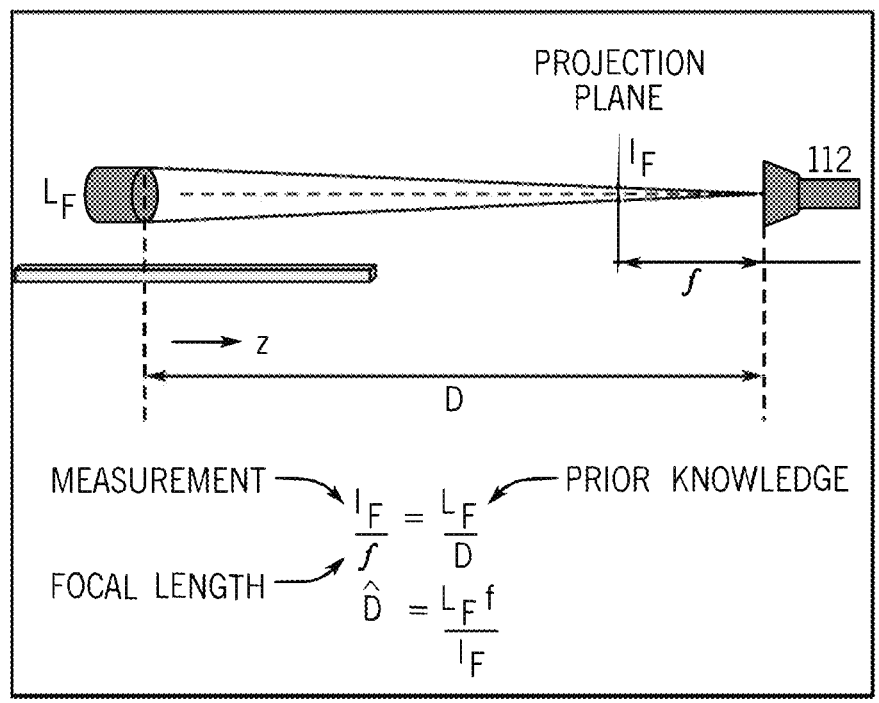
FIG. 6 shows a schematic relating a camera to a marker for position determination of the marker.

FIG. 6 shows a schematic with the calculations for 3D position determination based on a pinhole camera model. $L_F$ is the diameter of the marker in millimeters, $I_F$ is the diameter of the marker in pixels, and f is the focal length of the camera 112. Using this prior information and the measured diameter in pixels found in the image, the distance of the marker from the camera plane (D) in camera coordinates can be found. The x and y image coordinates of the marker are found by finding the center pixel of the marker in the image frame. The intrinsic matrix, K, is used to transform from the image coordinate system to the camera coordinates, and then the rotation matrix and translation vectors are used to transform from camera coordinates to world coordinates in order to find the 3D location of the marker with respect to the world origin, as represented by:

$$P_{camera} = D*[xy1]*K^{-1}$$

$$P_{world} = (P_{camera} - t)*R^{-1}$$

Other models may be used to determine the 3D positions of the markers from the 2D camera image. 3D imaging, such as a depth camera, may be used in other embodiments.

Returning to FIG. 5, the template attenuation coefficient map 508 of the local coil is fit 510 to the located markers. Any non-rigid fitting may be used, such as mutual information or intensity-based fitting. The fit warps or adapts the local coil into the 3D locations. For stiff local coils, a rigid fitting may be used.

The attenuation coefficient map may be integrated with a model that limits the fitting. Using a mathematical model of the coil that imposes known constraints on possible deformed states, the attenuation coefficient map template is fit to the marker points or locations. In an alternative embodiment, the template attenuation coefficient map is fit without limiting by the model. In yet other embodiments, multiple templates at different orientations and deformations are created. The template which is the closest match to the marker locations is used as the deformation to the markers or used to further deform to the markers. The location of best fit of that selected template provides the location. The end result is an attenuation or mu-map 516 representing the attenuation of the local coil as placed on or by the patient in 3D.

If the goodness of fit is below a predefined threshold, the data-driven PET approach based on consistency criteria may be used to refine the fit. The PET data 512 from PET scanning is used in the data driven fit 514 of the PET data to the template map.

In other approaches, the processor applies a machine-learned model to output the distribution of marker locations or attenuation in 3D. The distribution information is output from a machine-learned model in response to input of the optical information.

Figure 7:
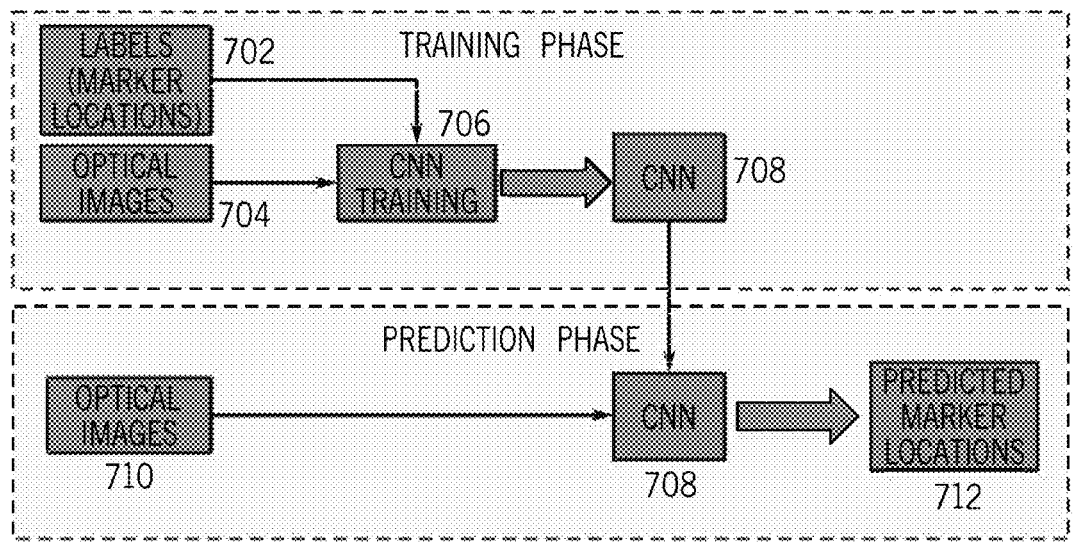
FIG. 7 illustrates an example deep learning-based approach for attenuation template fitting.

FIG. 7 shows one example where the machine-learned model outputs the marker locations 712. The 3D locations 712 of markers of the flexible local coil are predicted by a machine-learned model receiving the camera-captured image 710 as input. Various machine-learned models may be used, such as a neural network. For example, a convolutional neural network (CNN) 708 or fully connected neural network is trained with deep learning 706 to output the 3D spatial locations 712 of markers given an input optical image 710, such as a normalized or filtered optical image. To train 706 this network 708, multiple pairs of ground-truth marker locations 702 (e.g., determined automatically or manually from CT images) and corresponding 2D optical images 704 are used. In the prediction phase when a patient is being scanned and no ground-truth maker locations are known, the marker locations 712 are determined by the trained network 708 from the 2D optical image 710.

As discussed with respect to FIG. 5, the template attenuation coefficient map or local coil model is fit to the 3D locations. The 3D locations output by the machine-learned model are used to adapt the template attenuation coefficient map. For example, a mathematical model of the coil that imposes constraints on possible deformed states is fit to the 3D locations. Further refinement (e.g., PET consistency criteria method) may be provided, such if the goodness of fit is below a threshold.

Figure 8:
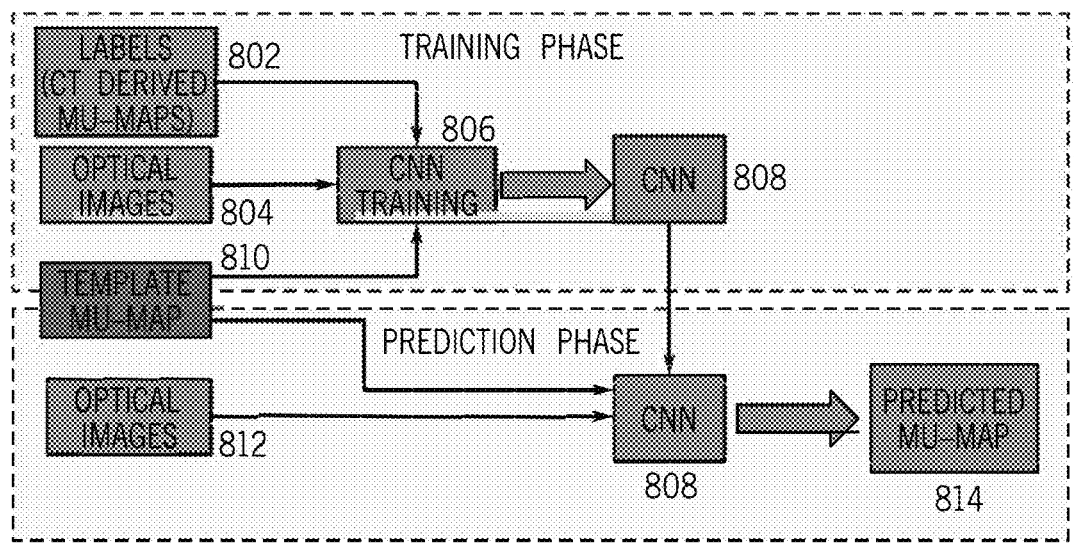
FIG. 8 illustrates an example deep learning-based approach for determining an attenuation distribution of MR hardware.

FIG. 8 shows one example approach where the machine-learned model outputs the adapted attenuation coefficient map. Rather than outputting the 3D locations, the machine-learned model directly outputs the 3D distribution of attenuation or the adapted attenuation coefficient map 814 as fit to the patient in response to receiving the image 812 as input. Various machine-learned models may be used, such as a neural network (e.g., CNN 808 or a fully connected network). The CNN 808 directly creates an attenuation coefficient map 814 of the coil on the patient from the 2D optical image 812. The template attenuation coefficient map 810 and/or other inputs may also or may not be provided to the CNN 808 as input. In the training phase, multiple pairs of ground-truth attenuation images (e.g. CT images 802) of the coil and corresponding 2D optical images 804 are used. Each pair of training data inputs represents the coil on the patient table in a different position. The template attenuation coefficient map 810 may also or may not be provided as an input. The CNN is trained 806 using deep learning. During the prediction phase when a patient is to be scanned and no ground truth attenuation image is known, the 2D optical image 812 is input to the CNN 808 with or without the template attenuation coefficient map 810 to deform or output the template attenuation image to the patient-specific instance, providing the predicted attenuation coefficient map 814 in 3D.

Different machine-learned models may be trained for different circumstances. For example, different machine-learned models are provided for different types of local coils. In this case, the template attenuation coefficient map 810 is not used. In another example, the CNN 808 is trained 806 to output the attenuation coefficient map 814 for different types of local coils, so the template attenuation coefficient map 810 for the local coil being used for a given patient may be used as an input but need not be used.

Referring again to FIG. 4, the PET imager performs PET imaging in act 406 using attenuation correction. The attenuation correction includes attenuation correction for the attenuation caused by the MR hardware or local coil. The attenuation coefficient map as adapted (deformed, oriented, and/or positioned) for the placement on the patient is used in the PET imaging. The attenuation correction may include attenuation correction factors for the patient tissues.

PET sinogram data is acquired. For example, time-of-flight (TOF) data for emissions detected along a plurality of lines of response is acquired. The acquisition is by scanning with the PET scanner. In alternative embodiments, the acquisition is by transfer or upload from a memory.

Gamma rays are detected by one or more rings of detectors or other grouping of detectors. The patient ingests or is injected with a radiopharmaceutical. The radiopharmaceutical includes an isotope. The isotope decays over time, resulting in generation of a positron, which forms gamma radiation or photons. Line-of-response events from a patient are detected. The acquisition occurs over any period. For example, the acquisition is over 1, 10, 100, or other number of minutes. The detected gamma rays are checked for coincidence to define lines-of-response, and the time difference or relative timing for coincident detections is recorded as prompt data. Any time window may be used for coincidence processing, such as 0.2 microsecond coincidence time window. Each detected emission event corresponds to a line or part of a line through a patient. By detecting emission events from different angles around a patient, a volume may be reconstructed.

An image object of the patient is reconstructed from the detected emission data for the lines of response. For example, the object space is reconstructed form the PET TOF, such as from prompt or sinogram data. Other PET detection and reconstruction may be used. The activity distribution in three dimensions is reconstructed. The activity distribution is used for imaging, such as volume rendering, multi-planar reconstruction, or planar imaging.

Any reconstruction may be used. In one embodiment, the reconstruction is a Poisson iterative reconstruction, such as a maximum likelihood reconstruction. OSEM, FORE, or other reconstructions may be used. The reconstruction estimates the object or patient space from the lines-of-response. The detected events are used to iteratively determine the object space using forward, backward, or forward and backward projection.

The reconstruction includes attenuation correction. Some of the lines of response pass through the MR hardware. The contribution of attenuation from the MR hardware (i.e., the correction factor based, at least in part, on the MR hardware) is used in the reconstruction. The 3D distribution of attenuation from the MR hardware is included in the attenuation correction factors for the lines of response passing through the 3D distribution. The distribution of the attenuation from the MR local coil is used in the attenuation correction of PET reconstruction. In one embodiment, at least a portion of the patient is reconstructed from emissions from the patient using attenuation correction. The attenuation coefficient map for the MR hardware is included with attenuation for the portion of the patient in the attenuation correction.

In PET imaging, an image is displayed. The reconstructed activity or emission distribution as an image object is used to create a PET image. An image is generated by reconstructing the object space and then rendering or imaging from the reconstructed object. The image is of the patient, such as a PET image showing function or uptake of the radiopharmaceutical. The image benefits from the attenuation correction for the MR hardware. More accurate imaging less sensitive to noise is provided.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for positron emission tomography (PET) imaging that accounts for attenuation by magnetic resonance (MR) hardware, the method comprising:

imaging a patient with an optical camera, the imaging capturing an optical image of the patient and the MR hardware;

generating an attenuation coefficient map for the MR hardware relative to the patient from the optical image; and performing the PET imaging using attenuation correction based, at least in part, on the attenuation coefficient map for the MR hardware.

2. The method of claim 1, wherein imaging comprises imaging one or more optical fiducials on the MR hardware, and wherein generating comprises determining a position of the MR hardware relative to the patient.

3. The method of claim 1, wherein generating comprises outputting the attenuation coefficient map as fit to the patient by a machine-learned model receiving the optical image as input.

4. The method of claim 1, wherein imaging the patient with the optical camera comprises imaging the patient with the optical camera and at least one additional optical camera, and wherein generating comprises generating the attenuation coefficient map from the optical image and at least one additional optical images from the at least one additional optical camera.

5. The method of claim 1, wherein generating comprises identifying one or more three-dimensional positions of the MR hardware from the optical image using a color-coded marker and/or a visible pattern on the MR hardware.

6. The method of claim 1, wherein performing comprises reconstructing at least a portion of the patient from emissions, the reconstruction using the attenuation correction where the attenuation coefficient map for the MR hardware is included with attenuation for the portion of the patient.

7. The method of claim 1, wherein imaging comprises imaging the patient with the camera outside a bore of a combination PET and MR imaging system, the camera directed to a patient bed of the combination PET and MR imaging system.

8. The method of claim 2, wherein imaging comprises imaging the patient while the patient is outside the bore.

9. The method of claim 1, wherein generating the attenuation coefficient map comprises generating the attenuation coefficient map of the MR hardware as positioned for the patient from a template map of attenuation of the MR hardware.

10. The method of claim 9, wherein the MR hardware comprises a flexible local coil, and wherein generating comprises adapting the template to reflect a positioning of the flexible local coil on the patient.

11. The method of claim 10, wherein adapting comprises recognizing shapes and locations of markers of the flexible local coil in the optical image, determining three-dimensional locations of the markers from the shapes and locations, and fitting the template to the three-dimensional locations.

12. The method of claim 10, wherein adapting comprises predicting three-dimensional locations of markers of the flexible local coil by a machine-learned model receiving the optical image as input, and fitting the template to the three-dimensional locations.

13. A medical imaging system comprising:
a positron emission tomography imager;
a magnetic resonance imager configured to image a patient using one or more local coils positioned on a patient;

a camera configured to capture an optical image of the patient and the one or more local coils as positioned on the patient; and a processor configured to correct for attenuation of the one or more local coils based on one or more positions, respectively, identified from the optical image, the correction being for imaging by the positron emission tomography imager.

14. The medical imaging system of claim 13, wherein the positron emission tomography imager and the magnetic resonance imager share a bore for imaging the patient and wherein the camera is mounted outside the bore and the optical image is captured while the patient is partially outside the bore.

15. The medical imaging system of claim 13, wherein the one or more local coils comprise flexible local coils, and wherein the processor is configured to identify the one or more positions as three-dimensional positions from markers on the one or more local coils.

16. The medical imaging system of claim 15, wherein the processor is configured to generate an attenuation coefficient map from a fit of template attenuation coefficient maps to the three-dimensional positions.

17. A method for positron emission tomography (PET) imaging that accounts for attenuation by a magnetic resonance (MR) local coil, the method comprising:

capturing an optical image of the MR local coil as positioned on the patient;

determining a distribution of attenuation from the MR local coil based on the optical image; and reconstructing a PET image from emissions, the reconstructing including attenuation correction using the distribution of the attenuation from the MR local coil.

18. The method of claim 17, wherein determining the distribution comprises locating markers on the MR local coil from the optical image and fitting an attenuation template to the located markers.

19. The method of claim 17, wherein determining the distribution comprises outputting distribution information from a machine-learned model in response to input of the optical information.

20. The method of claim 17, wherein determining comprises determining a deformation and position of the MR local coil as positioned on the patient for MR imaging, the distribution of attenuation being based on the deformation and position of the MR local coil.

* * * * *